United States Patent
Hartlep

(10) Patent No.: US 6,694,162 B2
(45) Date of Patent: Feb. 17, 2004

(54) NAVIGATED MICROPROBE

(75) Inventor: Andreas Hartlep, München (DE)

(73) Assignee: BrainLab AG, Kirchhem/Heimstetten (DE)

( * ) Notice: Subject to any disclaimer, the term of this patent is extended or adjusted under 35 U.S.C. 154(b) by 0 days.

(21) Appl. No.: 10/005,205

(22) Filed: Dec. 4, 2001

(65) Prior Publication Data
US 2003/0078485 A1 Apr. 24, 2003

(30) Foreign Application Priority Data
Oct. 24, 2001 (EP) .............................................. 0124379

(51) Int. Cl.$^7$ ................................................ A61B 5/04
(52) U.S. Cl. ...................................... 600/378; 600/373
(58) Field of Search ............................... 600/378, 373; 607/116; 128/899

(56) References Cited

U.S. PATENT DOCUMENTS

| | | | |
|---|---|---|---|
| 4,461,304 A | | 7/1984 | Kuperstein |
| 5,715,836 A | * | 2/1998 | Kliegis et al. ............... 128/898 |
| 5,776,064 A | * | 7/1998 | Kalfas et al. ................ 600/414 |
| 6,117,143 A | * | 9/2000 | Hynes et al. ................ 606/130 |
| 6,330,466 B1 | * | 12/2001 | Hofmann et al. ........... 600/378 |
| 2001/0027272 A1 | | 10/2001 | Saito et al. |

FOREIGN PATENT DOCUMENTS

| | | |
|---|---|---|
| WO | 98/39669 A | 9/1998 |
| WO | 01/49197 A | 7/2001 |
| WO | 01/76497 A | 10/2001 |

* cited by examiner

Primary Examiner—Michael Peffley
Assistant Examiner—Aaron Roane
(74) Attorney, Agent, or Firm—Renner, Otto, Boisselle & Sklar, LLP

(57) ABSTRACT

The invention relates to a device for electrophysiologically localizing target areas in the brain, comprising a multi-channel microprobe (10) which at its active end comprises a multitude of tightly packed microelectrodes arranged axially in rows, via which electrophysiological efferences are obtained in the target area and forwarded to an evaluating unit, wherein the microprobe (10) is assigned to a tracking device (5) which allows the microprobe (10) to be positionally detected by means of a neuronavigation system (1, 2, 3, 8) and the insertion of the probe to be stereotactically planned.

13 Claims, 2 Drawing Sheets

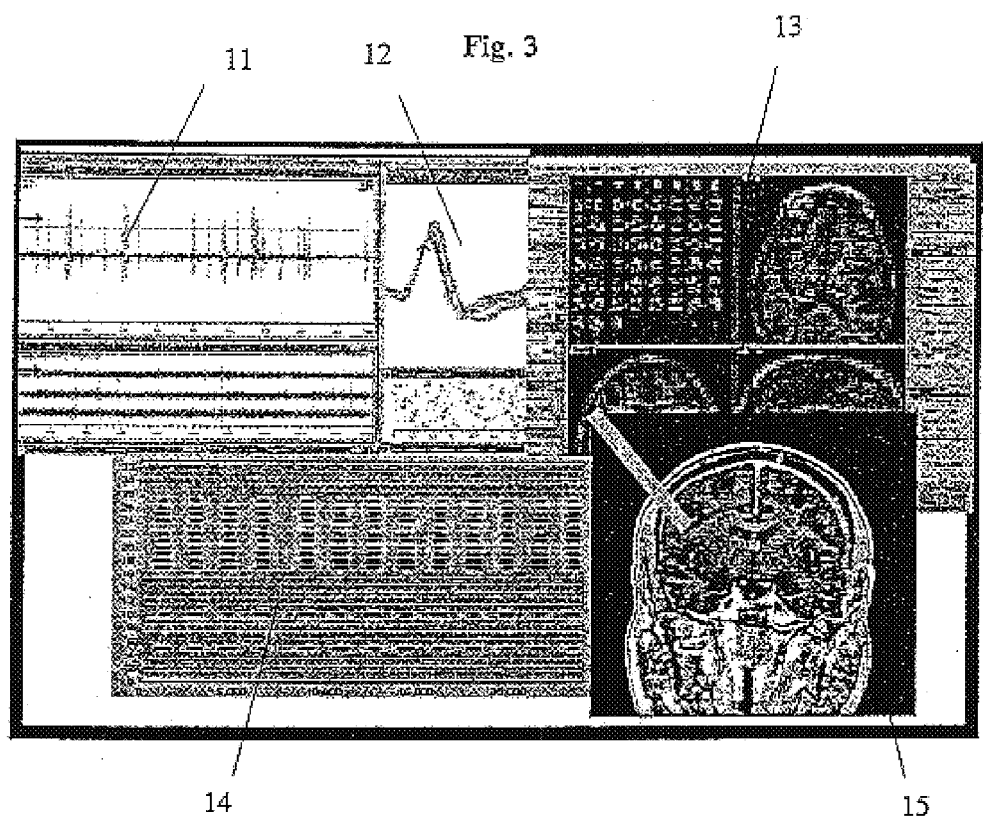

NAVIGATED MICROPROBE

TECHNICAL FIELD

The present invention relates to a device for electrophysiologically localising target areas in the brain, in accordance with the preamble of patent claim 1.

DESCRIPTION OF RELATED ART

With the increasing average age of the population in the industrial nations, the incidence of age-related illnesses is also growing. Parkinson's syndrome and essential tremor certainly figure among the most common and most debilitating illnesses here. Once medicinal treatments no longer show any success, such neurodegenerative illnesses are treated by brain surgery, the success of which is highly dependent on correctly determining the target area in the brain. For a while now, target areas have often been localised using electrophysiological efferences of the neuronal discharge pattern along a stereotactically given trajectory. For this purpose, multi-channel microprobes are used which are inserted into the patient's brain by means of a manipulator and which at their active end comprise a multitude of tightly packed microelectrodes arranged axially in rows, via which electrophysiological efferences are obtained in the target area. Exactly determining the target in this way is extremely important, for a misplaced therapeutic measure can have serious side effects for the patient. Performing a pallidotomy on a Parkinson's patient is cited here as an example, wherein a misplaced coagulation electrode would result in irreversible damage to the tractus opticus in the immediate vicinity of the pallidum. Alongside the continuing Parkinson's symptoms, the patient in question would then additionally suffer from a possibly considerable restriction of his vision.

Admittedly, functional areas in the brain can in principle be localised with the aid of hitherto known microprobe localising techniques, however even experienced brain surgeons require a number of processes with a test probe to obtain a reasonably correct image of the layers of the structure of the target areas. It is however also known from practice many brain surgeons have little or no experience of identifying areas from their specific activities. According to the level of difficulty, such a traditional approach, introducing the probe a number of times, lasts between 6 and 20 hours. For a large part of this time, the patient has to be conscious, so the success of the electrical stimulation can be checked by way of absence of the illness. A further disadvantage are of course the repeatedly necessary penetrations of the substance of the brain.

With respect to the prior art regarding microprobes and medical navigation systems (see below), reference is made to the following documents: U.S. Pat. Nos. 5,855,801; U.S. 5,843,148; U.S. 5,833,709; U.S. 5,800,535; U.S. 5,782,645; U.S. 5,755,759; U.S. 5,713,922; U.S. 5,524,619; U.S. 5,524,338; U.S. 5,496,369; U.S. 5,411,540; U.S. 5,388,577; U.S. 5,215,088; U.S. 4,969,468; U.S. 4,890,623; U.S. 4,837,049; U.S. 4,461,304.

SUMMARY OF THE INVENTION

It is the object of the present invention to provide a device for electrophysiologically localising target areas in the brain, which does not exhibit the disadvantages cited above. In particular, a high precision of the target finding method in the sub-millimeter range is to be achieved, and the surgeon is to be given fundamental and comprehensible assistance in using the captured efference data.

This object is solved in accordance with the invention by assigning the microprobe a tracking device which allows the microprobe to be positionally detected by means of a neuronavigation system. In particular, this has the advantage that with such a device, electrophysiological localising can be planned and also carried out with a much higher initial precision by means of the microprobe, and thus with a smaller number of insertion processes and in much shorter time. The number of required trajectories is minimised, which also makes the localising process as a whole minimally invasive. Neuronavigation offers various options both in calculating the target co-ordinates and in operative surgery. The target is localised on the one hand by physiologically identifying the target area by means of the microprobe, and on the other by anatomical navigation.

In a preferred embodiment of the present invention, the navigation system comprises a screen output on which the evaluations of electrophysiological localization and of the navigational data are shown together. The electrophysiological data in question (such as efferences or spike frequencies) can then be shown for the surgeon, together with anatomical image data available to the navigation system, in a unified representation and including a databank. This improves the operating technique, and the risk to the patient is minimized. Neuronavigation systems, such as are known for example from DE 196 39 615 C2, work with patient data recorded beforehand by tomographic imaging methods, for example CT or MR recording methods. Via the screen output, images reconstructed from these data can be displayed together with images of the microprobe itself and its results data, and the surgeon can then compare the peak model of the electrophysiological navigation, which offers an individual neurone resolution, with the image information and with theoretical knowledge, to exactly determine the position of the microprobe or of a microelectrode on it. The invention thus combines the two localizing methods into navigation with high resolution using a user-friendly and easy-to-use user interface.

In accordance with an advantageous embodiment, the microprobe has 25 to 32 microelectrodes. If 32 tightly packed microelectrodes are present at the active end of the microprobe, it is possible to pass through a target area completely and relatively quickly with the microprobe and then to simultaneously derive nerve signals as neuronal discharge from each of the 32 microelectrodes patterns from various brain centre segments.

In accordance with an embodiment in accordance with the invention, the navigation system is an optical navigation system, the tracking device being attached to a manipulator for the microprobe and consisting of an arrangement of markers, in particular of three reflection markers, whose spatial position is detected by cameras of the navigation system.

On the other hand, it is possible to provide magnetic navigation, i.e. a navigation system which is designed as a magnetic navigation system, the tracking device being attached to a manipulator for the microprobe or to the microprobe itself and consisting of an arrangement of coils, in particular of two miniature coils, whose spatial position is detected in an established magnetic field.

In the two cases cited above, it is advantageous if the navigation system further comprises a patient tracking device, by means of which a current position of the patient's head can be detected in real time, such that movements of the patient do not have a disruptive or precision-blunting effect on navigation or localisation.

The two localising systems, namely the electrophysiological localising system with the microprobe and the neuronavigation system, can supplement each other and so provide synergistic effects. Thus, the device in accordance with the invention is on the one hand advantageously designed such that the navigation system comprises a computer unit which links the data from the electrophysiological efferences of functional areas of the brain, the advance of the probe and the navigational data with one another and adapts navigation by way of positional data and information from the electrophysiological efferences of functional areas of the brain. In this way, the navigation system can benefit from the very high precision of electrophysiological localisation, and other anatomical points can be very exactly assigned by way of this precise information. A second option is to design the device in accordance with the invention such that the navigation system comprises a computer unit which links the data from the electrophysiological efferences of functional areas of the brain and the navigational data with each other and works positional data and information from the electrophysiological efferences of functional areas of the brain into the anatomical data available to the navigation system. In this way, for example, a "virtual brain atlas" for the given patient can be produced, which is available for later treatments or diagnoses.

In general terms, the present invention makes it possible to detect specific functional areas of the brain, either for conventional surgery, for a so-called deep brain simulation (DBS) or for neurological examinations. In this sense, the invention also relates to the methods described herein, while simultaneously using multi-channel microprobes and a navigation system, wherein visualising and equalising the databank with image data produced beforehand from tomographic imaging methods have the advantageous effect of combination.

BRIEF DESCRIPTION OF DRAWINGS

The invention will be explained in the following in more detail by way of a preferred embodiment. The drawings show:

FIG. 3 a way of representing the signals obtained using the device in accordance with the invention on a screen output.

DETAILED DESCRIPTION OF THE INVENTION

Figure 1:
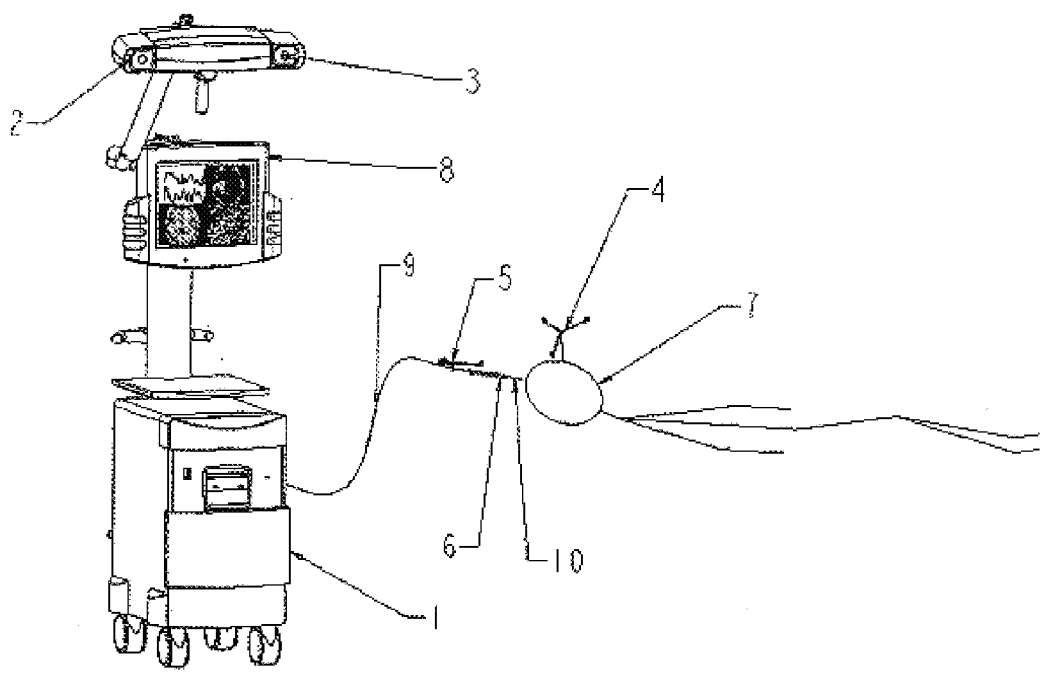
FIG. 1 a schematic view of a navigation and localisation system in accordance with the invention.

FIG. 1 is a schematic representation of a combined navigation and localisation system comprising a device in accordance with the invention. The neuronavigation system is shown on the left in the image, said system comprising as its main components the navigational computer 1, the screen 8 and the camera support with the cameras 2 and 3. This optical navigation system can track arrangements of markers, and therefore also the objects fitted with these arrangements of markers. In the present case, these objects are a microprobe 10 arranged on a microprobe manipulator 6 which in turn bears an arrangement of markers 5 consisting of three markers spaced from each other. Another arrangement of markers 4 is fixed to a patient's head, the head in FIG. 1 having the reference numeral 7. A cable 9 runs from the microprobe manipulator 6 to the navigational computer 1, wherein the cable 9 transfers the measuring results of the microprobe 10 to the computer system. The microprobe manipulator 6, and therefore the microprobe 10, can be tracked, i.e. positionally followed, in the detection area of the cameras 2 and 3 via the arrangement of markers 5 arranged on the microprobe manipulator 6. The position of the probe in relation to the anatomy of the patient can then be shown on the screen 8, if anatomical data on the area of the patient's head have been captured beforehand by means of a tomographic imaging method. The patient and the microprobe and/or the manipulator 5 are registered in a known manner before treatment, and in order to rule out errors due to movement of the patient's head, these movements are also detected by means of the arrangement of markers 4 and worked into the navigation.

The tracked microprobe 10 can then be inserted into the patient's head with the assistance of the navigation system, i.e. with a predetermined trajectory, to electrophysiologically localise the target areas of interest, i.e. the functional areas. In this way, the navigation system can propose a trajectory on the screen unit 8 and also display deviations of the actual course from the planned course, such that even on the first insertion, the probe can be relatively precisely positioned.

Figure 2:
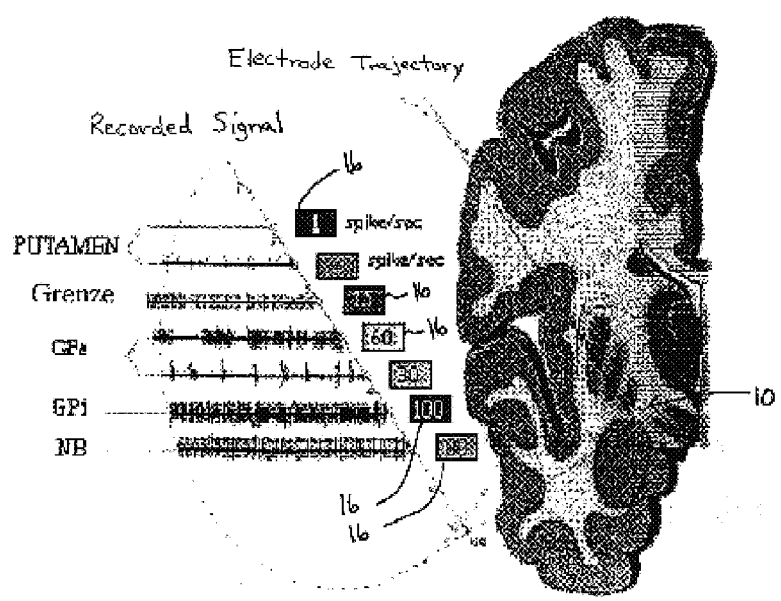
FIG. 2 an example of deriving a signal at a microprobe inserted into the brain.

FIG. 2 shows an example of the course of a probe on a brain tomograph. If the probe 10 is inserted with the trajectory shown (the line in the brain section), neurone signals can be derived at the microelectrodes 16 situated at the active end of the probe, which are shown as an example in the left-hand half of the image in FIG. 2 in an enlarged representation.

Neuronavigation offers various options both in calculating the target co-ordinates and in operative surgery. The target is localised on the one hand by physiologically identifying the target area by means of the microprobe, and on the other by anatomical navigation. There are again various options here, which can be combined in any way.

Firstly, an insertion is planned by way of a line through two anatomical structures (for example, the commissura anterior et posterior); this is planned by means of the anatomical positional data available in the neuronavigation system. Furthermore, a virtual brain atlas can for example be laid over the patient's brain, which is likewise carried out by means of neuronavigation planning. Moreover, the target can be directly visualised in appropriate structures, if for example corresponding images are available for example from suitable MR imaging sequences of the brain. These options in combination achieve a precision of the target area localisation in the millimeter range. Using these co-ordinates, the electrode can then be placed in the brain by a mechanical target device directly screwed into the cranium of the awake patient. Using neuronavigation, it is thus possible to approach the target area precisely with a very small attachment on the cranium, and to perform a minimally invasive operation. The image-led checking of the progress of the operation can be improved further by electrophysiological measurements.

In accordance with the structure of the brain, the function efferences of neurone activity allow the position of the microprobe to be concluded. Here, the microprobe consists of a fine microelectrode with a diameter of 0.1 mm in the interior of a jacket tube, said microelectrode being brought nearer and nearer to the target area by electrophysiological efferences. The advance of this microelectrode is constantly communicated to the navigation system, such that the "z" co-ordinate of the tip of the probe can be measured and displayed with high precision. The target region is thus revealed with high precision not only by the calculated position on the images but also by the specific activity patterns.

This test probe can then be retracted back into a jacket tube and the non-insulated end of the jacket tube used as a stimulation probe. Simulation by a weak electrical stimulus is on the one hand positive evidence that the correct inhibitory area has been identified, but on the other is also necessary, for example, in order to not come too close to the optic nerve. Once the apparently correct co-ordinates have been identified in the brain, a new electrode is introduced, and the target area is burnt away up to a diameter of several millimeters.

The surgeon can be assisted by the representation of the navigation and localisation results on the screen output during the treatment as a whole. An example of such a screen output is shown in FIG. 3. Here, the screen is sub-divided into a number of open windows, such that the information of interest to the surgeon is also available to him simultaneously.

In the present case, the screen view in FIG. 3 shows a spike template 12, a single channel representation 11, a navigational map 13, a target map 15 with the trajectory, and a 32-channel derivation 14. With the aid of this combined image output, it is possible for the surgeon—as already indicated above—to plan his surgery carefully and to carry it out under guidance, by means of topographically assigning the neuronal discharge patterns derived in the central nervous system by sub-partitioning the various basal nuclei and/or the functionally or anatomically definable segments with micrometer precision, in the sense of microsomatotopy. Alongside an increase in the localisation precision of the target area, such an integrated navigation and localisation system also drastically shortens the operation time. This results in less strain on the patient's health and also lower costs.

What is claimed is:

1. A device for electrophysiologically localizing a target areas in the brain, said device comprising:
    a multi-channel microprobe including:
        a multitude of microelectrodes said microelectrodes being operative to obtain electrophysiological efferences in the target area and forwarded the electrophysiological efferences to an evaluating unit; and
        a tracking device;
    a neuronavigation system operative to positionally detect the microprobe via the tracking device and thereby localize the target area; and
    a computer unit that links data indicative of the electrophysiological efferences of functional areas of the brain and navigational data with one another and outputs the linked data.

2. The device as set forth in claim 1, further comprising:
    a screen output on which evaluations of electrophysiological localization and navigational data are shown together.

3. The device as set forth in claim 1, wherein the microprobe (10) includes 25 to 32 microelectrodes.

4. The device as set forth in claim 1, wherein the computer unit links data indicative of the electrophysiological efferences of functional areas of the brain and navigational data with one another and adapts navigation by way of positional data and information from the electrophysiological efferences of functional areas of the brain.

5. The device as set forth in claim 1, wherein the tracking device includes an arrangement of reflection markers.

6. The device as set forth in claim 5, wherein the neuronavigation system includes a patient tracking device for detecting a current position of a patient's head in real time.

7. The device as set forth in claim 5, wherein the tracking device includes an arrangement of three reflection markers.

8. The device as set forth in claim 5 wherein the neuronavigation system is an optical navigation system including at least one camera for detecting spatial positions of the arrangement of reflection markers.

9. The device as set forth in claim 1, wherein the tracking device includes an arrangement of coils.

10. The device as set forth in claim 9, wherein the tracking device includes an arrangement of at least two miniature coils.

11. The device as set forth in claim 9, wherein the neuronavigation system is a magnetic navigation system for detecting spatial positions of the arrangement of coils.

12. The device as set forth in claim 1, wherein the computer unit links data indicative of the electrophysiological efferences of functional areas of the brain and navigational data with each other and works positional data and information from the electrophysiological efferences of functional areas of the brain into anatomical data available to the neuronavigation.

13. The device as set forth in claim 12, wherein the computer unit links data indicative of the electrophysiological efferences of functional areas of the brain and navigational data with each other and works positional data and information from the electrophysiological efferences of functional areas of the brain into anatomical data available to the navigation system for producing a brain atlas.

* * * * *

UNITED STATES PATENT AND TRADEMARK OFFICE
CERTIFICATE OF CORRECTION

PATENT NO. : 6,694,162 B2
DATED : February 17, 2004
INVENTOR(S) : Andreas Hartlep It is certified that error appears in the above-identified patent and that said Letters Patent is hereby corrected as shown below:

<u>Column 5,</u>
Line 39, replace "areas" with -- area --
Line 41, insert -- , -- after the first occurrence of "microelectrodes".
Line 43, replace "forwarded" with -- forward --.
Line 20, insert -- , -- after "5".

Signed and Sealed this

Fifteenth Day of June, 2004

JON W. DUDAS
*Acting Director of the United States Patent and Trademark Office*